(12) United States Patent
Lambert et al.

(10) Patent No.: US 7,469,718 B2
(45) Date of Patent: Dec. 30, 2008

(54) QUICK DISCONNECT CRYOGENIC COUPLER

(75) Inventors: Todd Dennis Lambert, Brooklyn Park, MN (US); Shawn David Ellis, Golden Valley, MN (US); Mario Alejandro Calvo, Minneapolis, MN (US)

(73) Assignee: Parker-Hannifin Corporation, Cleveland, OH (US)

( * ) Notice: Subject to any disclaimer, the term of this patent is extended or adjusted under 35 U.S.C. 154(b) by 510 days.

(21) Appl. No.: 11/186,539

(22) Filed: Jul. 21, 2005

(65) Prior Publication Data

US 2006/0022464 A1    Feb. 2, 2006

Related U.S. Application Data

(60) Provisional application No. 60/591,288, filed on Jul. 27, 2004.

(51) Int. Cl.
*F16L 37/28* (2006.01)
(52) U.S. Cl. .......................... 137/614.04; 137/614.03; 251/149.6; 62/50.7; 285/904
(58) Field of Classification Search ............ 137/614.03, 137/614.04, 614.05; 62/50.7; 285/47, 904; 251/149.1, 149.6
See application file for complete search history.

(56) References Cited

U.S. PATENT DOCUMENTS

| | | | |
|---|---|---|---|
| 3,842,614 A | 10/1974 | Karcher et al. | |
| 5,265,844 A | 11/1993 | Westfall | |
| 5,363,879 A | 11/1994 | Rhoades | |
| 5,429,155 A | 7/1995 | Brzyski et al. | |
| 5,647,398 A * | 7/1997 | Giesler | 137/614.03 |
| 5,779,244 A * | 7/1998 | Moriarty et al. | 277/311 |
| 5,880,043 A | 3/1999 | Lorenz et al. | |
| 6,047,553 A | 4/2000 | Germain | |
| 6,079,446 A | 6/2000 | Tocha | |
| 6,145,322 A | 11/2000 | Odashima | |
| 6,539,970 B1 | 4/2003 | Knowles et al. | |
| 7,111,641 B2 * | 9/2006 | Marban et al. | 137/614.03 |
| 7,117,892 B2 * | 10/2006 | Krywitsky | 137/614.04 |

* cited by examiner

*Primary Examiner*—Kevin L Lee
(74) *Attorney, Agent, or Firm*—Joseph J. Pophal; Daniel J. Whitman

(57) ABSTRACT

A generally cylindrical quick disconnect female cryogenic coupler, interconnected with a cryogenic fluid transfer apparatus, includes a coupler body with a first cavity housing a laterally severed tubular bushing, an adaptor having one end attached to the coupler body and another end to the apparatus, a normally closed-biased valve between the coupler body and the adaptor, a coupling sleeve, attached to the coupler body having, a frusto-conical inlet portion, and a vent fitting having one end connected with a coupling sleeve radial aperture and another end in operative connection with a cryogenic fluid storage vessel, associated with the noted apparatus, to permit the inlet purging by using the vessel's own gaseous phase as a purging medium during liquid fluid transfer operation. The severed bushing inhibits ice formation, at an inlet/male nipple interface during the noted transfer. A method for purging moisture at the noted interface is also set forth.

30 Claims, 8 Drawing Sheets

QUICK DISCONNECT CRYOGENIC COUPLER

CROSS-REFERENCE TO RELATED CASE

The present application claims the benefits of the filing date of U.S. Provisional Application No. 60/591,288, filed Jul. 27, 2004.

BACKGROUND OF THE INVENTION

1. Field of the Invention

The present invention pertains to quick disconnect couplers operatively inter-connected with a cryogenic liquid fluid transfer apparatus and associated with a cryogenic fluid storage vessel. Specifically, the invention pertains to the use of a laterally severed tubular bushing that serves to inhibit ice formation, at a coupler inlet/male nipple interface during liquid fluid transfer. In addition, a vent fitting, having one end attached to radial aperture in a coupling sleeve inlet portion, and another end in operative connection with the cryogenic storage vessel, permits inlet purging by using the vessel's own gaseous phase as a purging medium during the liquid fluid transfer operation.

Quick disconnect couplers are well known and are utilized in every conceivable type of fluid transfer application. One of the intended types of end products utilizing the quick disconnect cryogenic coupler of the present invention are portable liquid oxygen units. Such units, in one application, are typically used by patients suffering from Chronic Obstructive Pulmonary Disease (COPD) and provide them with oxygen. In such an apparatus, liquid oxygen, stored in a small cryogenic dewer, is converted to breathable gas, via a warming mechanism, thereby providing the patient with warmed $O_2$ at a given pressure and flow rate. For such applications, the portable cryogenic dewers are filled from larger stationary refill tanks, with the cryogenic coupler of this invention being utilized in such cryogenic liquid fluid transfer apparatuses. It should be understood that cryogenic couplers are also utilized in other cryogenic applications, not just at the end product, but also at the end of fluid transfer apparatuses, such as hoses, tubing or ducting, and with Liquid Natural Gs (LNG) couplings and the like.

In terms of the operation, the male half of the coupling, namely the nipple, is inserted into the female half of the coupling, namely the coupler. Internal valves in both halves are opened as the coupler and nipple are united, with a complete coupling connection therebetween constituting the "coupling". Once both internal valves are open, liquid fluid is allowed to flow from the nipple into and through the coupler. Once the desired amount of fluid has passed through the coupling, the two halves are pulled apart, with this disconnection process also allowing the two internal valves to shut, thereby preventing any further fluid transfer through the coupler.

Cryogenic fluid transfer, due in large part to the great difference in the ambient temperature and that of the fluid being transferred, involves icing, due mainly to condensation, particularly at the nipple/coupler interface. One known method of reducing such icing is to utilize a thermal break angle, between the nipple and coupler, by incorporating, in the sleeve of the coupler, of an about 10 degree change in its inlet diameter, thereby allowing a thermal break during the noted refill process. Such a construction allows an air break between the coupler and the nipple, thus preventing ice from freezing the two halves together.

Another known way for reducing ice formation between the two coupling halves is the use of a purge mechanism, such as a purging medium, e.g., an external purge gas, such as compressed air. Such purging does remove moisture but requires an additional, external supply of a purging medium.

2. Description of the Related Art

The patent literature sets forth a large number of cryogenic coupling constructions, some of which include: U.S. Pat. No. 3,842,614 to Karcher et al.; U.S. Pat. No. 5,265,844 to Westfall; U.S. Pat. No. 5,363,879 to Rhoades; U.S. Pat. No. 5,429,155 to Brzyski et al.: U.S. Pat. No. 5,880,043 to Lorenz et al.; U.S. Pat. No. 6,047,553 to Germain; U.S. Pat. No. 6,079,446 to Tocha; U.S. Pat. No. 6,145,322 to Odajima; and U.S. Pat. No. 6,539,970 B1 to Knowles et al. However, none of these prior art structures include the use of a laterally severed tubular bushing that functions as an anti-freezing lining inside the coupler, relative to the adjoining nipple portion. In addition, all of the prior art structures utilize an external source for a purge medium, not the purging gas emanating from the unit being charged or refilled with the liquid phase of the purging gas.

SUMMARY OF THE INVENTION

Accordingly, in order to overcome the deficiencies of the prior art devices, the present invention provides a quick disconnect coupler that includes the use of a laterally severed bushing that functions as an anti-freezing lining inside the coupler, relative to an adjoining nipple portion. In addition, the purging medium utilized in removing moisture from the coupler/nipple interface is the own internal gas that is purged from the unit being charged or refilled with the liquid phase of the same composition.

Specifically, in terms of structure, in this invention, a quick disconnect coupler, operatively interconnected with a cryogenic fluid transfer apparatus, the coupler comprising in combination: a. a generally cylindrical coupler body having a through bore and a front cylindrical portion with a first cavity open on one end, separated from a rear portion with a second cavity open on another end, via an apertured intermediate wall portion perpendicular on a first side facing the first cavity and including a tapered wall portion on a second side facing the second cavity; b. the first cavity having an inner peripheral surface surrounding an outer peripheral surface of a laterally severed tubular bushing, with the condition of being severed permitting a predetermined amount of radial expansion of the bushing; c. a generally tubular adaptor having a second through bore and a cylindrical rear portion, operatively attached to the cryogenic fluid transfer apparatus, a cylindrical, apertured, intermediate portion including a valve guide, located in the through bore, and a cylindrical front portion sealingly, operatively, connected with to the coupler body rear portion; d. an annular interface seal, spaced from the coupler body intermediate wall portion, the spacing of the seal permitting a limited amount of axial movement of the tubular housing; e. a valve, normally biased to a closed position, interposed between the valve guide and the coupler body tapered wall portion, with a valve head portion shutting the apertured intermediate wall portion in the closed position thereof; and f. a generally tubular coupling sleeve having a frusto-conical front inlet portion separated from a cylindrical outlet portion via an annular end face adjoining the front inlet portion, the coupling sleeve being operatively secured to the coupler body front portion, with the annular end face physically abutting the first cavity.

In one version, the severed tubular bushing is comprised of a polymeric composition material, preferably of one of a PTFE composition material and PTFE equivalent material composition.

In another version, the tubular bushing is severed from one peripheral edge to the other peripheral edge in a diagonal manner, preferably in the form of a scarf-cut.

In a further version, the outside diameter of the tubular bushing is radially spaced, a predetermined distance, from the inner peripheral surface of the first cavity inner peripheral surface, so as to permit a predetermined amount of radial movement therebetween.

In still another version, the frusto-conical front inlet portion of the coupling sleeve further includes a radial aperture, with this aperture being operatively connected with one end of a vent fitting, with another end of the fitting being in an operative connection with a cryogenic fluid storage tank of a cryogenic device associated with the cryogenic fluid transfer apparatus.

In a variation of the above version, the operative connection with the cryogenic fluid storage tank includes a flow control valve, with the flow control valve preferably being associated with the cryogenic fluid storage tank.

In another variation of the above version, the operative connection with the cryogenic fluid storage tank is at a position in the tank that is filled with a gaseous fluid, with the operative connection of the coupling sleeve front inlet portion with the cryogenic fluid storage tank of the cryogenic device permitting the purging of the inlet portion by utilizing the cryogenic device's own gaseous fluid as the purge mechanism, in the form of a moisture remover, during the cryogenic liquid fluid transfer operation.

A differing version further includes a male nipple assembly releasably joined with the coupler via an operative interconnection.

In one variation the preceding version, the operative interconnection includes, in the nipple assembly, an inner end portion adapted to be inserted into the coupler via the coupler sleeve inlet portion and making a sealing contact with the inner peripheral surface of the annular interface seal, the severed bushing, via the limited amounts of axial radial movements, aiding in the prevention of icing, at the sealing contact, during the cryogenic liquid fluid transfer operation.

In another variation of the preceding version, the coupling front inlet portion further includes a radial aperture, the aperture being operatively interconnected with one end of a vent fitting, with another end of the vent fitting, in turn, being in an operative interconnection with a cryogenic fluid storage vessel of a cryogenic device associated with the cryogenic fluid transfer apparatus. The operative interconnection of the coupling sleeve inlet portion with the cryogenic fluid storage vessel permits the purging of the inlet portion and the adjacent nipple inner end portion by utilizing the cryogenic device's own gaseous fluid as the purging medium, in the form of moisture removal, during the cryogenic liquid fluid transfer operation.

In a further variation of the preceding version, the operative interconnection further includes, in the outer peripheral surface of one of the coupling sleeve and coupler body, at least one, radially outwardly-directed, cylindrical pin, the at least one pin being adapted to releasably mate, in a twisting motion, with one of at least one bayonet slot, formed in a cup member concentric and connected with the nipple assembly inner end portion.

In a differing variation of the preceding version, the operative interconnection with the cryogenic fluid storage vessel is at a position in the vessel that is filled with the gaseous phase of the cryogenic liquid fluid therein.

In another embodiment of the present invention, in a quick disconnect coupler and male nipple assembly combination, associated with a cryogenic fluid transfer apparatus, there is set forth a method for purging moisture from the interface of a coupling sleeve inlet portion and an adjacent nipple inner end portion, the method comprising the steps of: a. providing the inlet portion, at the interface, with a radial aperture; b. connecting one end of a vent fitting with the aperture; c. operatively connecting another end of the fitting with a cryogenic fluid storage vessel of a cryogenic device also associated with the cryogenic fluid transfer apparatus; and d. utilizing the cryogenic device's own gaseous fluid as a purging medium, for removing moisture, at the interface, during the cryogenic liquid fluid transfer operation.

In another version, the previous method further includes: e. locating one end of the operatively connecting step at a position in the storage vessel that is filled with the gaseous phase of the cryogenic liquid fluid residing therein.

In a further version, the method also includes: f. interposing a flow control valve between the vent fitting and the cryogenic fluid storage vessel.

In a differing version, the method additionally includes: g. opening the flow control valve during the cryogenic liquid fluid transfer operation; and h. closing the flow control valve upon cessation of the transfer operation.

Another embodiment of this invention pertains to a quick disconnect coupler, operatively interconnected with a cryogenic fluid transfer apparatus, the coupler comprising in combination: a. a generally cylindrical coupler body having a through bore and a front cylindrical portion with a first cavity open on one end, separated from a rear portion with a second cavity open at another end, via an apertured intermediate wall portion perpendicular on a first side facing the first cavity and including a tapered wall portion on a second side facing the second cavity; b. the first cavity surrounding an outer peripheral surface of a tubular bushing; c. an annular interface seal, located at one axial end of the bushing, permitting a limited amount of axial movement of the bushing; d. a generally tubular adaptor having a second through bore and a cylindrical rear portion, operatively attached to the cryogenic fluid transfer apparatus, a cylindrical, apertured, intermediate portion including a valve guide, located in the through bore, and a cylindrical front portion sealingly, operatively connected to the body rear portion; e. a valve, normally biased to a closed position, interposed between the valve guide and the coupler body tapered wall portion, with a valve head portion thereof shutting the apertured intermediate wall portion in the closed position; f. a generally tubular coupling sleeve having a frusto-conical front inlet portion separated from a cylindrical outlet portion via an annular end face adjoining the front inlet portion, the coupling sleeve being operatively secured to the coupler body front portion, with the annular end face physically abutting the first cavity; and g. a vent fitting having one end thereof connected with a radial aperture in the coupling sleeve front inlet portion, and another end of the vent fitting being in an operative connection with a cryogenic fluid storage vessel associated with the cryogenic fluid transfer apparatus, wherein the operative connection permits purging of the inlet portion by utilizing the cryogenic vessel's own gaseous phase as a purging medium, for moisture removal, during the transfer operation.

In one version thereof, the operative connection between the coupler and the cryogenic fluid storage vessel includes a flow control valve, with the flow control valve being associated with the cryogenic fluid storage vessel.

In another version thereof, the operative connection with the cryogenic fluid storage vessel is at a position in the vessel that is filled with a gaseous phase of the cryogenic fluid.

A differing version thereof, further includes a male nipple assembly releasably joined with the coupler via a further operative interconnection, with the further operative connection includes, in the nipple assembly, an inner end portion adapted to be inserted into the coupler via the coupler sleeve inlet portion and making a sealing contact with the inner peripheral surface of the annular interface seal and permitting the purging of the inlet portion and the adjacent nipple inner end portion. The tubular bushing is severed from one peripheral edge to the other peripheral edge in other than a direct lateral cut. The bushing is preferably scarf-cut, the cut aiding in the prevention of icing at a sealing contact between the inner peripheral surface of the annular interface seal and the adjoining male nipple portion, with the scarf-cut tubular bushing preferably being comprised of a polymeric material of a PTFE composition or a PTFE equivalent-type composition.

In yet a further version thereof, the outside diameter of the severed tubular bushing is radially spaced, a predetermined distance, from the inner peripheral surface of the coupler body first cavity, so as to permit a predetermined amount of radial movement therebetween.

DETAILED DESCRIPTION OF THE INVENTION

Figure 1:
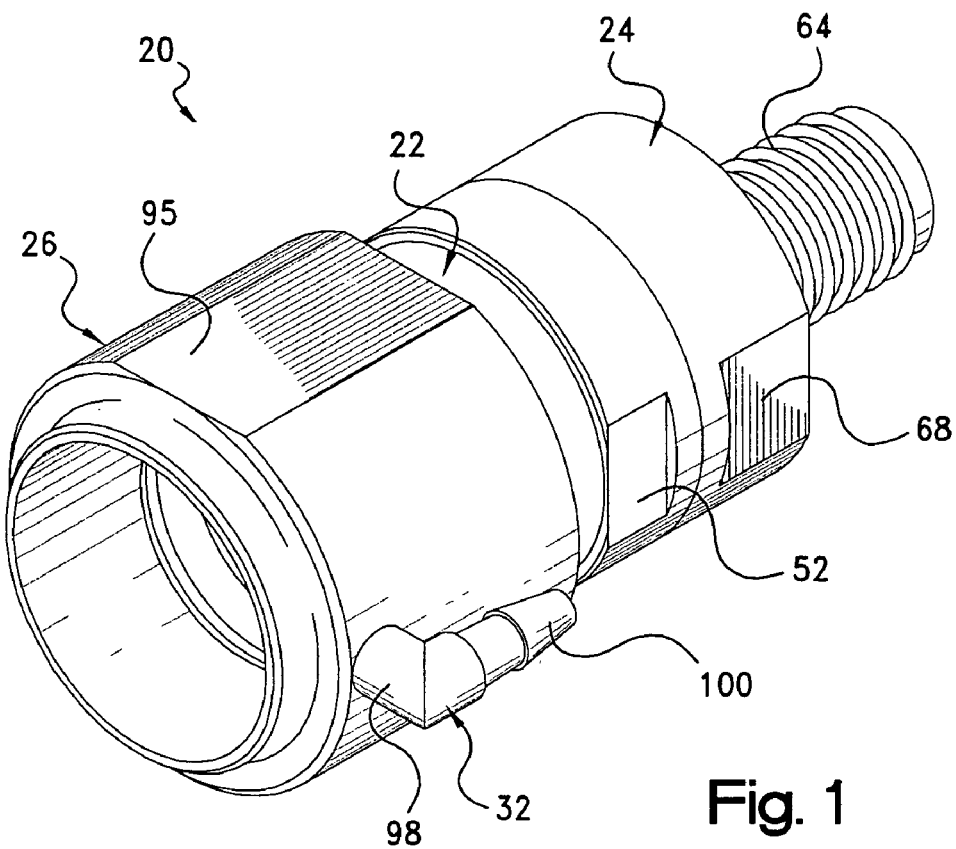
FIG. 1 is a perspective view of a first embodiment of a quick disconnect cryogenic coupler of the present invention.
Figure 2:
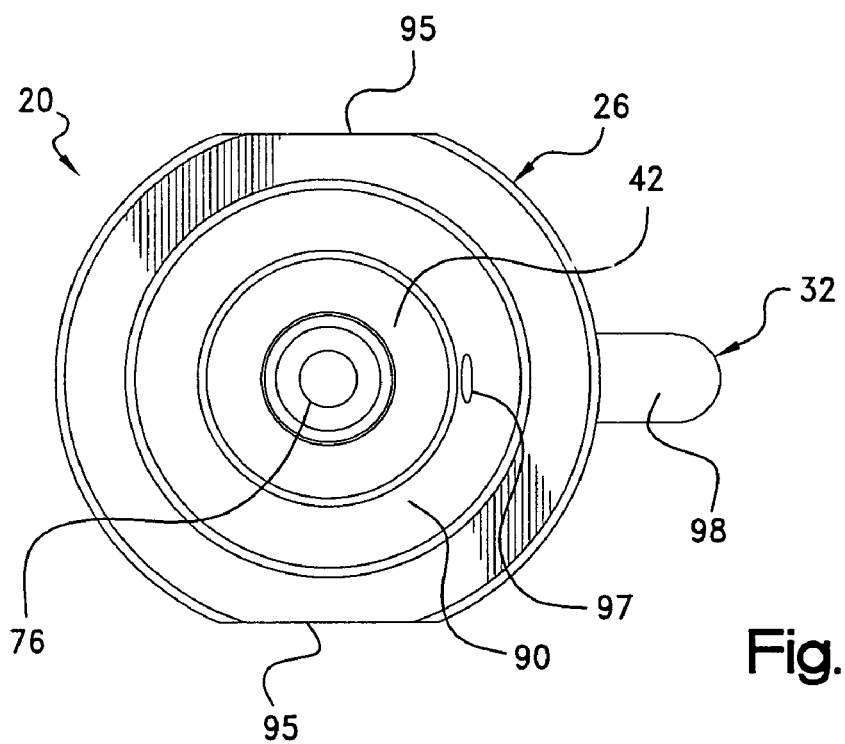
FIG. 2 is a view of the coupling end of the coupler of FIG. 1.

Referring now to the several drawings, illustrated in FIGS. 1-4 is a first embodiment of the quick disconnect cryogenic coupler of the present invention, generally indicated at 20, with coupler 20 being basically comprised of the combination of at least five major components, namely: a coupler body 22, an adaptor 24, a coupling sleeve 26, a valve assembly 28, a split bushing 30 in coupler body 22; and an optional vent fitting 32 in coupling sleeve 26. Coupler 20 is adapted to be releasably connected with any desired, known, male nipple (not shown in this embodiment) in order to transfer the cryogenic fluid. It should be understood that with coupler 20, no separate device is utilized to for locking same to the male nipple, rather, coupler 20 is physically held onto the male nipple with an external force being applied to the unit (FIG. 9) in which coupler 20 is installed.

Specifically, coupler body 22, which is generally cylindrical in shape, has an exterior threaded portion 34 and a cylindrical first or front cavity 36, in a front portion 35, separated from a rear or second cavity 38, in a rear portion 37, by an apertured intermediate wall portion 40 that is perpendicular on the side 42 facing first cavity 36 and frusto-conically tapered on the side 44 facing second cavity 38. Second cavity 38 includes an internally threaded cylindrical portion 48 and an end recess shoulder area 50 and may also include opposing exterior tool or wrench-receiving flat portions 52.

Adaptor 24, which is generally tubular in shape, has a reduced diameter externally-threaded cylindrical front portion 56 adapted to mate with coupler body internally threaded portion 48, and an adjoining recess shoulder area 58 which cooperates with coupler body shoulder area 50 to receive and confine a flexible seal member 62, to produce a leak-free environment therebetween. The interior of threaded front portion 56 defines a third cavity 60 that partially coincides with second cavity 38. An exterior threaded rear portion 64 is separated from front portion 56 via a larger diameter generally cylindrical intermediate portion 66 having opposed external tool or wrench-receiving portions 68. Rear portion 64 is adapted to be fixedly secured to a cryogenic vessel or tank 106, at about mid-height thereof, in the manner schematically shown in FIG. 9, which will be discussed in detail later. Adaptor 24 is further provided with a multi-diameter through bore 70 that includes an apertured valve guide 72, preferably in the form of a bridge, perch, or spider member, in adaptor intermediate portion 66 that serves to seat one end of a known or conventional valve assembly 28. Valve guide 72 may be formed integrally with adaptor 24 or inserted thereinto as a separate part. Valve assembly 28 includes a central stem portion 74 having a head portion 76 and a retainer portion 78, with an annular polymer seal 80, preferably of a PTFE or PCTFE, etc. composition being interposed therebetween, and a coil spring 81 for normally biasing seal 80 into a sealing relationship with coupler body frusto-conical wall portion 44.

Figure 3:
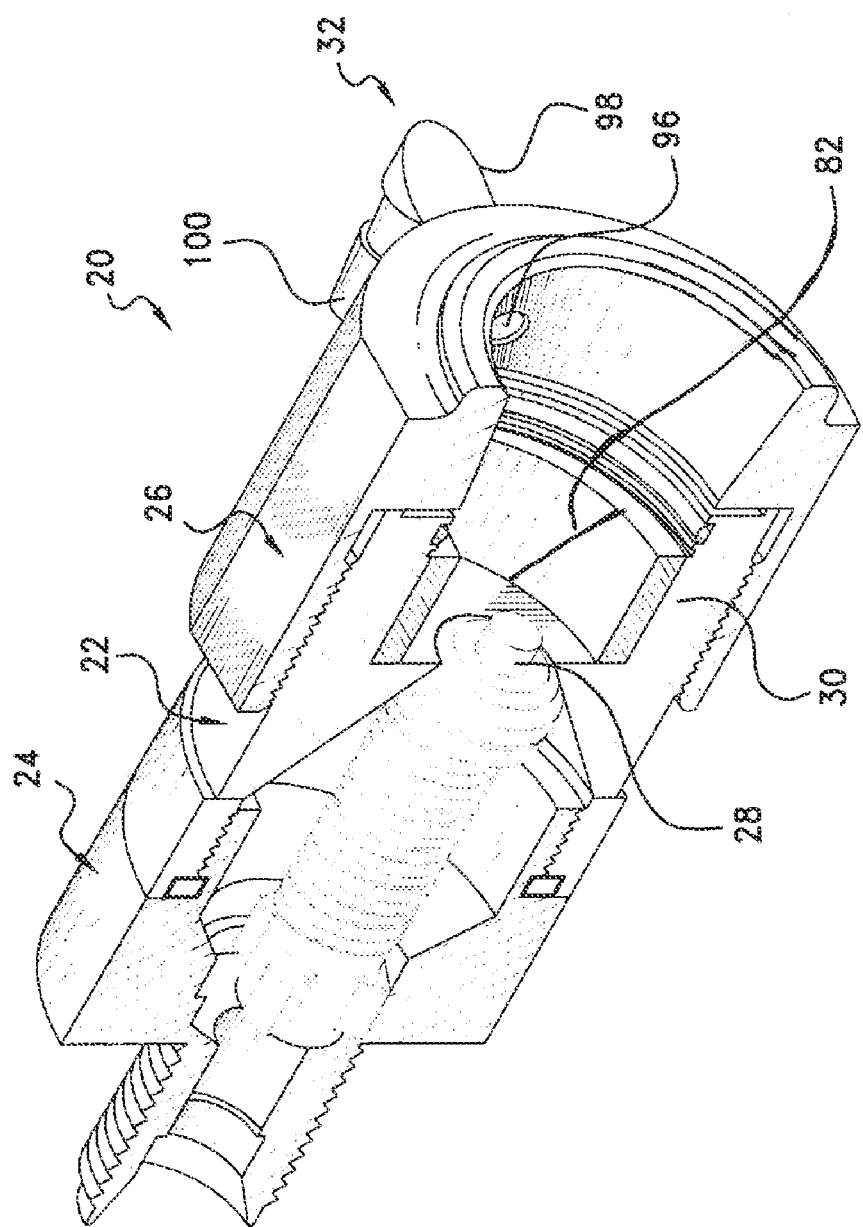
FIG. 3 is a view, similar to that of FIG. 1 but partly in section for the sake of clarity.
Figure 4:
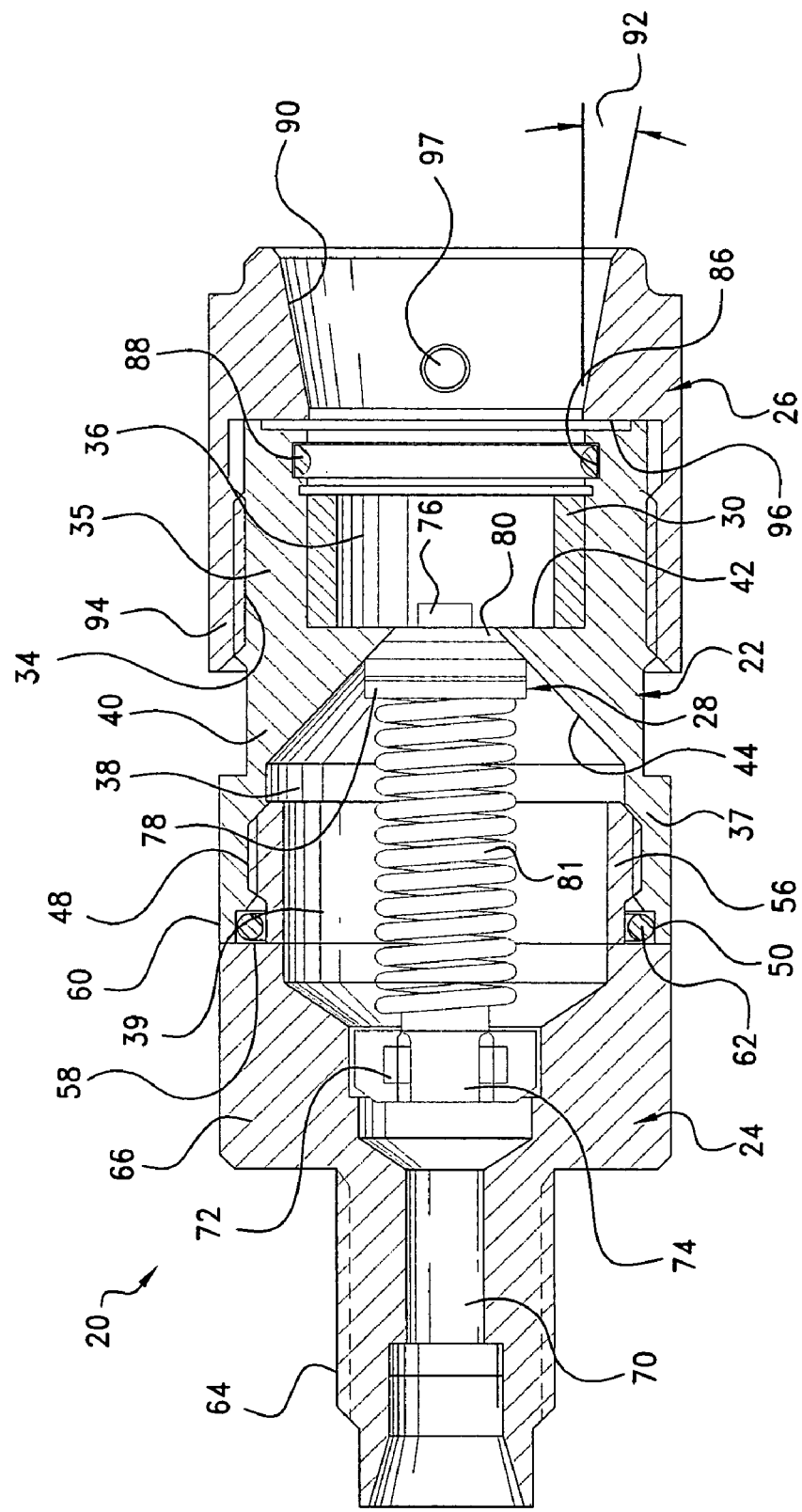
FIG. 4 is s vertical, longitudinal, side view, partly in section, similar to that of FIG. 3.

Returning now to coupler body 22, the inner peripheral surface of its front or first cavity 36 is provided with an anti-icing, slit, tubular, bushing 30, that is severed, e.g., by slicing or cutting axially across one side, from one edge to the other, preferably, but not limited to, in a diagonal manner 82 as shown in FIG. 3, with this type of cut often being referred to as a "scarf-cut". Such a cut 82 allows bushing 30 to diametrically or radially move and/or expand over the male nipple (not shown here) and/or any ice build-up thereon, while being disconnected from coupler 20. While scarf-cut technology is currently used for seals and back-up rings, etc., the use thereof in this invention now incorporates and expands this technology to anti-icing bushings utilized for cryogenic liquid transfer and filling of cryogenic fluid holding containers or vessels, often referred to as "dewers". In addition, the outside diameter of bushing 30 is radially spaced, a predetermined distance, from the inner peripheral surface of first cavity 36, so as to permit a predetermined amount of radial movement therebetween. Cut bushing 30 may be constructed of any desired material but is preferably constructed of a polymer material, such as PTFE or equivalents thereof, and is installed during the assembly of coupling 20. Bushing 30 may be loosely axially confined within cavity 36 in any known manner or method, e.g., via a known annular seal member 86 of any desired composition or material, e.g., of a polymeric composition, with seal member 86 preferably being retained in a recess 88 in cavity 36. As best seen in FIG. 4, the placement of seal member 86 allows for some limited axial movement thereof within cavity 36.

Figure 9:
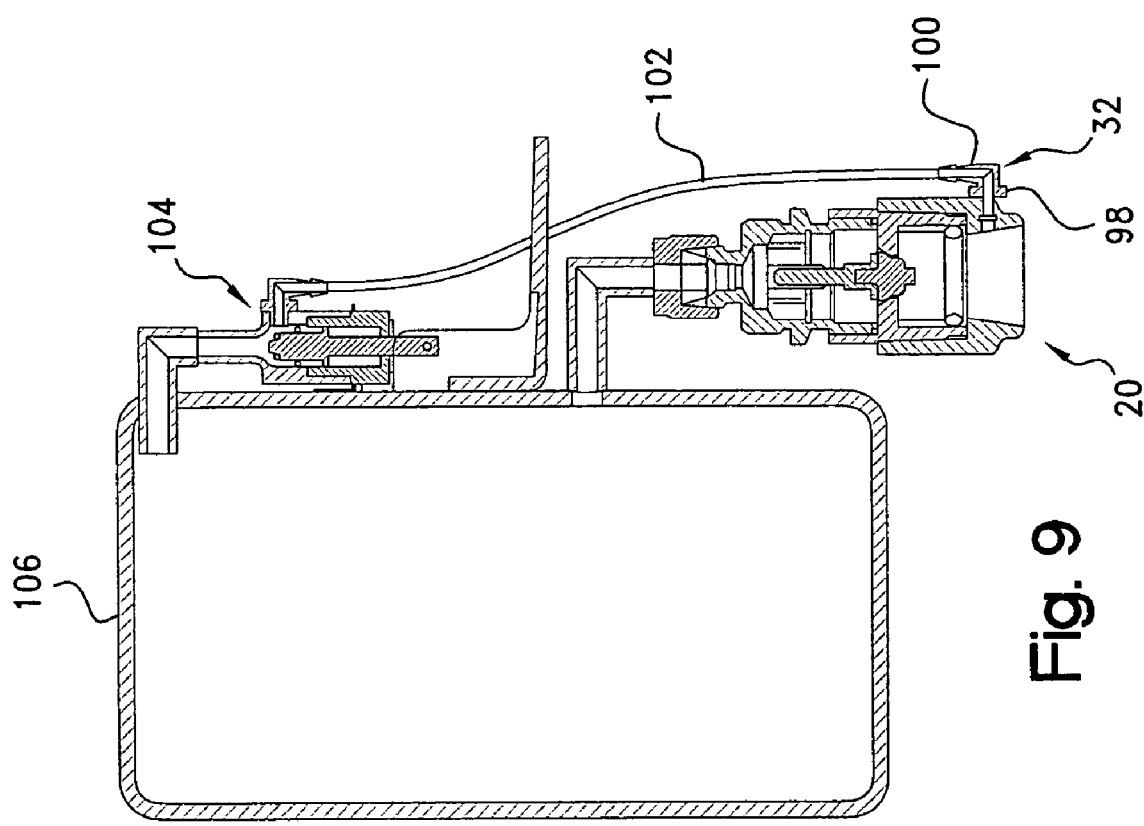
FIG. 9 is a schematic layout, mainly in section, of a tank of a portable cryogenic device, e.g. for holding liquid oxygen, or the like, shown during refill, which is the mode of operation thereof in which the quick disconnect couplers of the present invention can be utilized.

Turning now to coupling sleeve 26, which is of a generally tubular shape, it includes a front or inlet diameter frustoconical portion 90 having a known, tapered break angle 92, e.g., of an about 10 degree change in inlet diameter, allowing a thermal break during the refill process. This construction permits an air break between coupler 20 and the male nipple, thereby preventing ice from freezing these parts together. The outer peripheral surface of sleeve 26 may be provided with opposed tool or wrench-receiving flat surfaces 95. A generally cylindrical, internally-threaded, outlet portion 94 of sleeve 26 is separated from inlet diameter portion 90 via an annular end face 96, which, upon assembly with coupling body 22 operatively abuts cavity 36. Inlet diameter portion 90 is also provided with a radial aperture 97 that is adapted to fixedly receive one end 98 of vent fitting 32, with the other end 100 thereof being adapted for connection, via a hose/conduit/line 102, with any type of a desired, known, flow control valve 104, e.g., a manually-operated vent valve, which, in turn, is operatively connected with a cryogenic tank or dewer 106, preferably close to its maximum vertical height, as schematically shown in FIG. 9. It should be understood that, depending upon the type of application, the use of a valve 104 may not be necessary since this internal source of gas that is being utilized as a purging gas can be directly routed from tank 106 to coupler 20.

FIG. 9 illustrates valve 104 in its open position which allows the use of gas, vented from tank 106, during filling thereof, via cryogenic coupler 20, to purge moisture from the coupler/nipple interface. Thus, vent line 102, from valve 104, is connected to coupling sleeve 26, thereby permitting the use of the normally vented gas, from the inside of dewer 106, to aid in moisture removal at the noted interface. Upon the cessation of the filling cycle or operation, valve 104, is shifted or returned to its closed position.

In terms of the assembly of coupler 20, coupler body 22, adaptor 24 and coupling sleeve 26 are threaded together and act as a single unit in the finished assembly. Valve assembly 28 is captured or confined in the facing cavities of coupler body 22 and adaptor 24 and acts as the fluid shut-off device upon the disconnection of the male nipple. Anti-icing slit bushing 30 is installed in coupler body 22 during the assembly of coupling 20 and is held in place, e.g., by seal member 86 or the like.

In terms of the operation of coupler 20, the previously noted male half, or nipple (not shown), is inserted into coupler sleeve inlet diameter portion 90. During this insertion, internal valves, such as valve 28, in both halves are opened as coupler 20 is pushed further onto the nipple, with a complete connection between coupler 20 and the nipple providing a "coupling" therebetween. At this time, if moisture removal, at the coupler/nipple interface is desired, valve 104 is manually moved from its normally closed position, to its open position, thereby permitting the use of the gas being vented from dewer 106 to aid in moisture removal at the noted interface. With both internal valve halves or valve portions open, fluid is allowed to flow from the nipple into and through coupler 20. When the amount of desired fluid flow has passed through the coupling, valve 104 is returned to its normally closed position. Subsequently, the coupler and nipple halves are pulled apart. This "disconnection" process also allows the noted internal valves to close or shut, thereby preventing any further fluid transfer through coupler 20.

Figure 5:
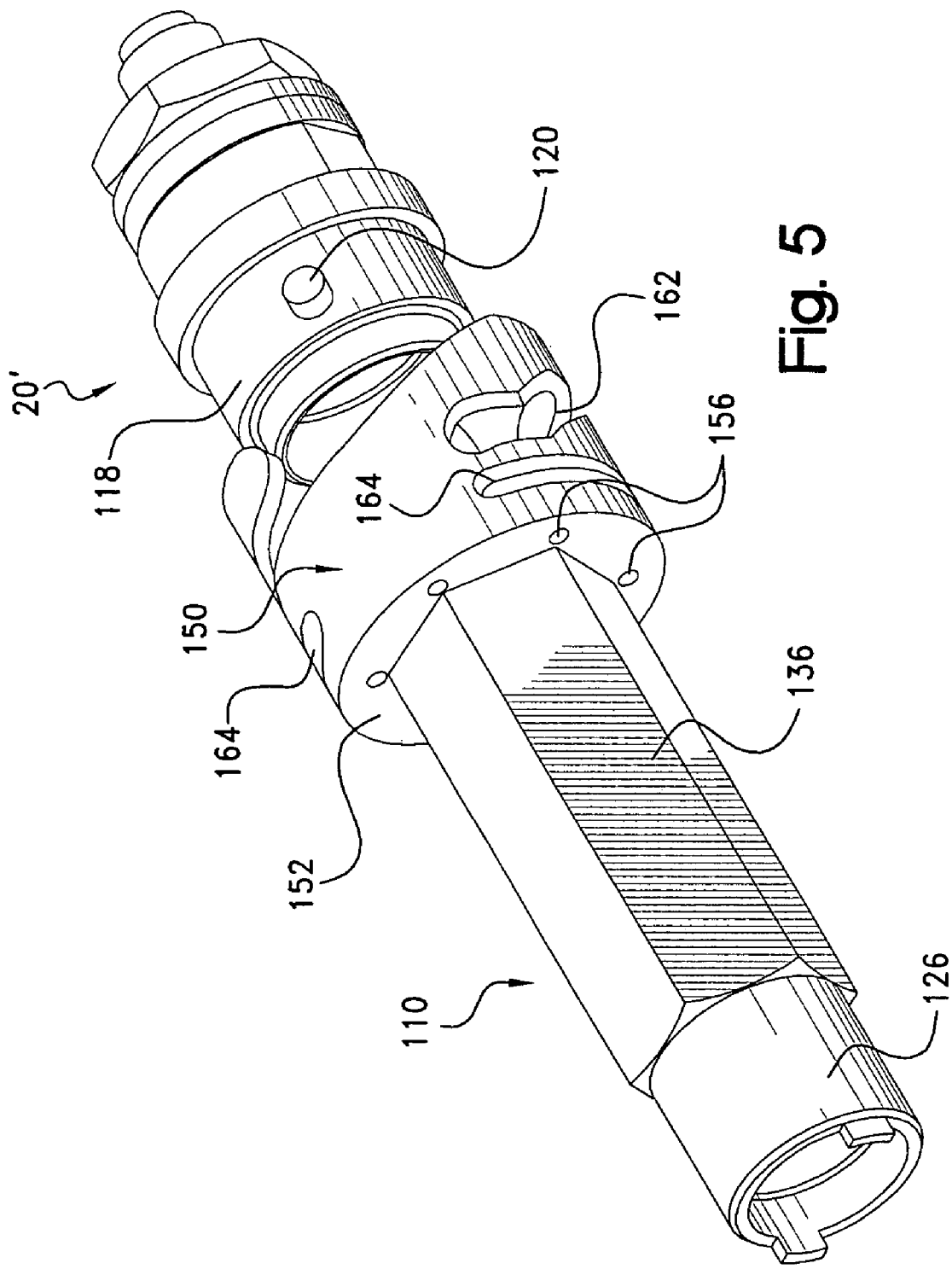
FIG. 5 is a perspective view of a second embodiment of a quick disconnect cryogenic coupler of the present invention, adjacent to a known nipple, shown in an uncoupled position.
Figure 6:
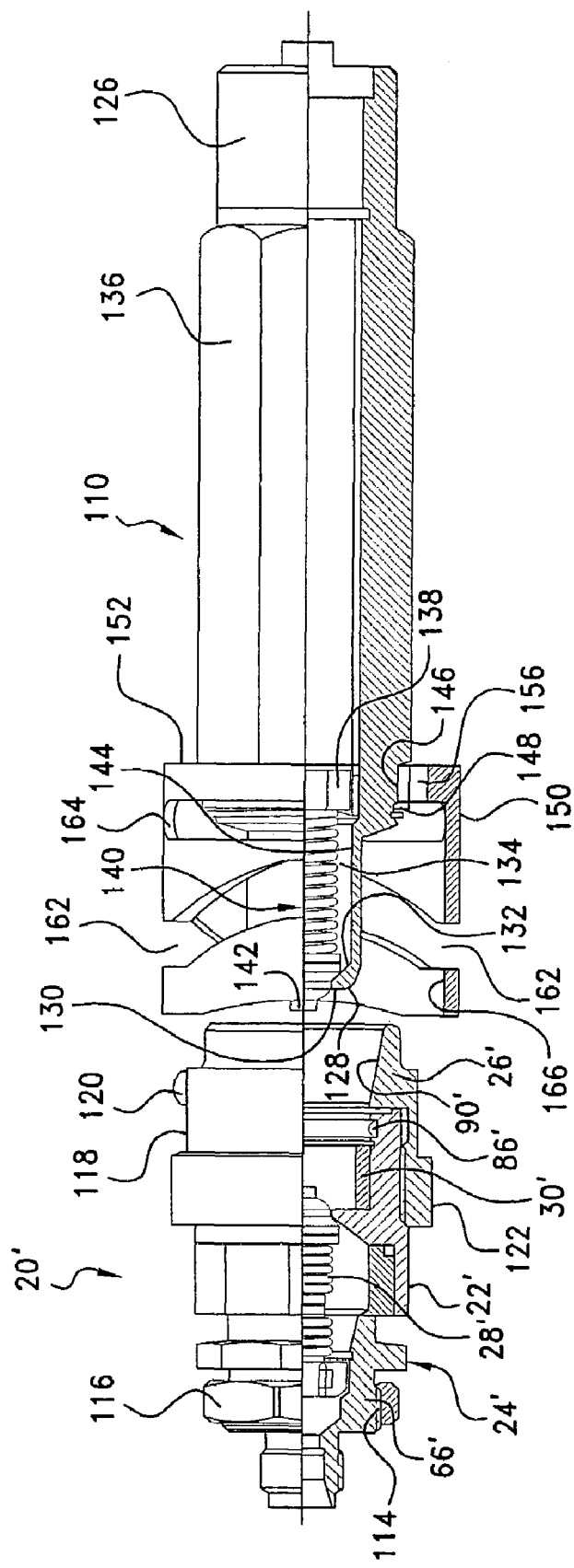
FIG. 6 is a vertical, longitudinal, side view, partly in section, of the FIG. 5 coupler and adjacent nipple, in the uncoupled position.
Figure 7:
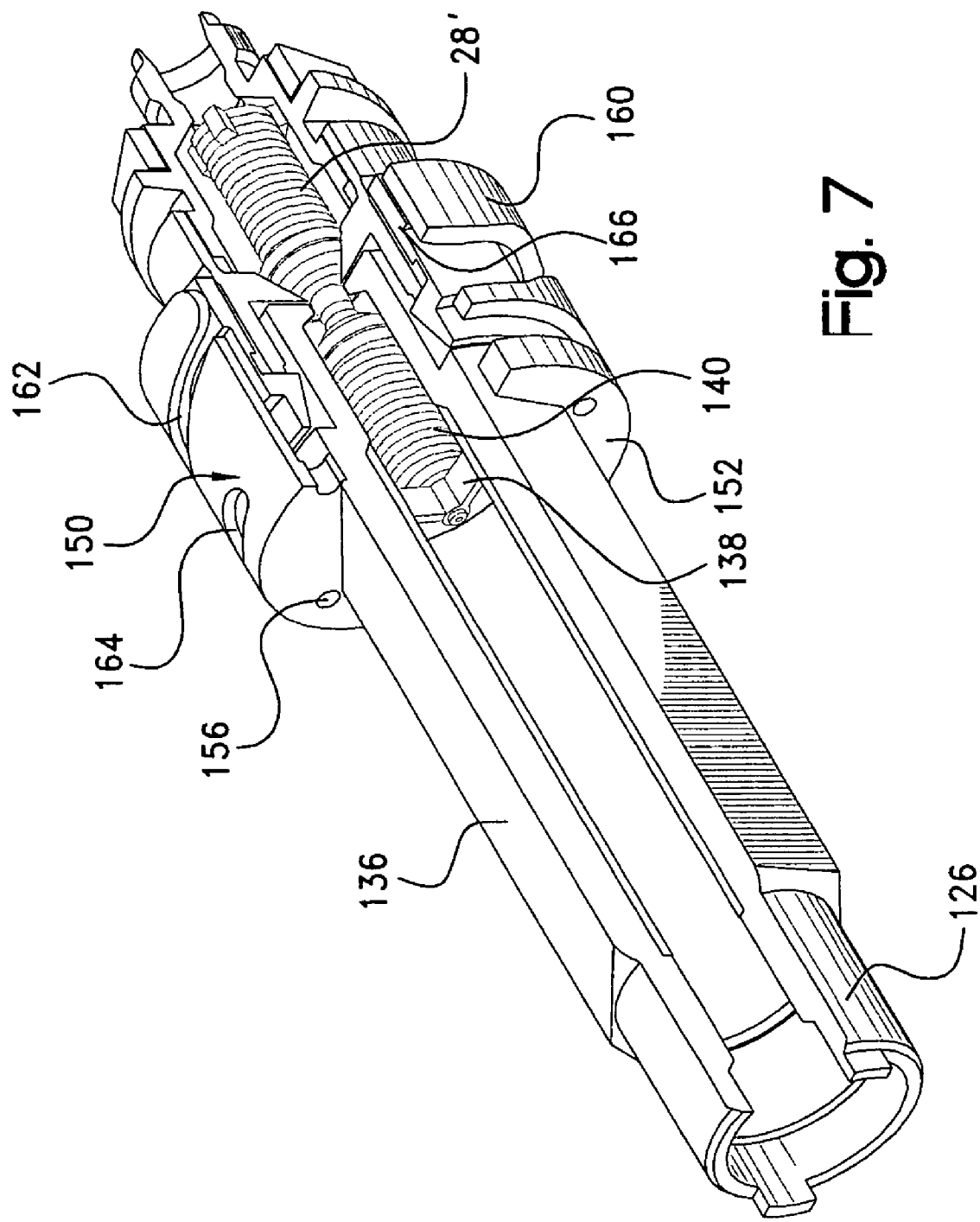
FIG. 7 is a perspective view, similar to that of FIG. 5, but partly in section, of the second embodiment of the quick disconnect coupler of the present invention, shown in a coupled position with the known nipple.
Figure 8:
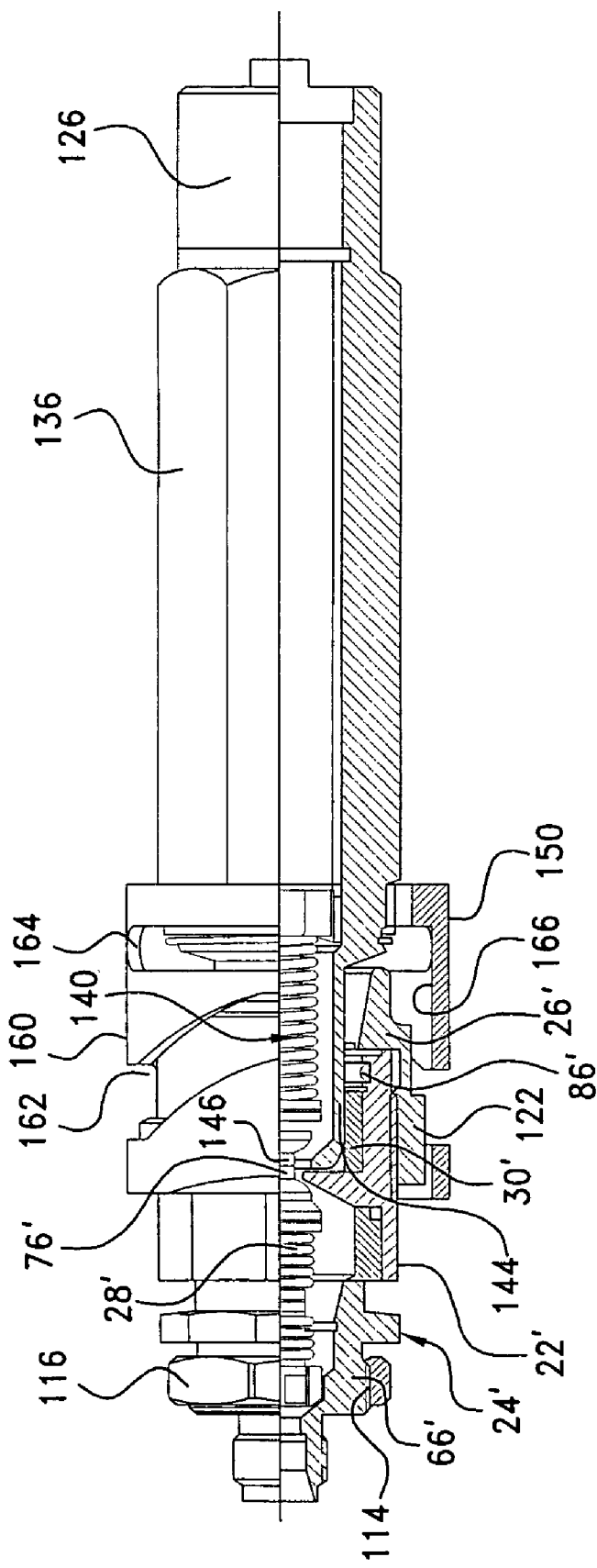
FIG. 8 is a vertical, longitudinal, side view, similar to that of FIG. 6 but showing the coupled position.
Figure 10:
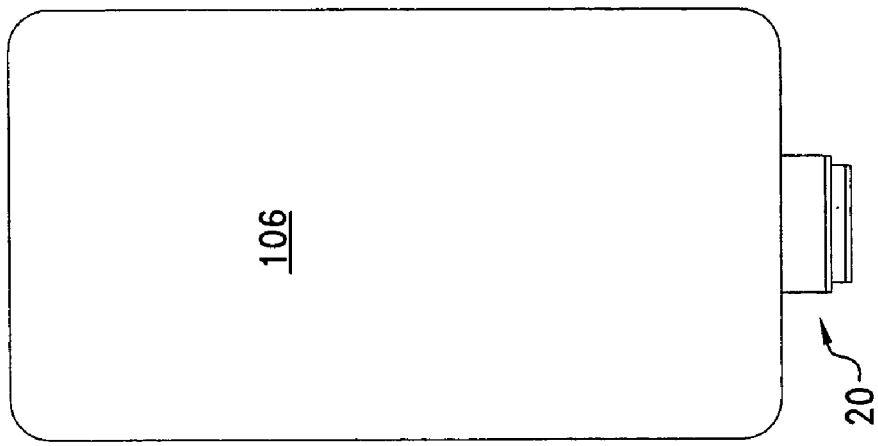
FIG. 10 is a rotated side view of the tank of FIG. 9.

Continuing now with FIGS. 5-8, illustrated therein is a second embodiment of the quick disconnect cryogenic coupler of the present invention, generally indicated at 20'. FIGS. 5 and 6 illustrate coupler 20' and a nipple assembly 110 in the uncoupled position, whereas FIGS. 7 and 8 illustrate same in the coupled position. Coupler 20' is similar to coupler 20, with like parts being denominated with the same numeral and the addition of a prime (') superscript as a suffix.

Specifically, coupler body 22' together with cut bushing 30' and seal member 86' is substantially similar to coupler body 22, bushing 30 and seal member 86. Adaptor 24' differs from adaptor 24 only by the addition, to intermediate portion 66', of an exterior threaded portion 114 and a complementary nut member 116. Coupler sleeve 26' differs from coupler sleeve 26 mainly in that coupler 26' has a generally tubular outer peripheral surface 122 that includes a recessed diameter frontal portion 118 that is provided with at least one and preferably a pair of opposite, radially outwardly-directed, boss portions or pins 120 (only one of which is shown) that are adapted to mate, in a twisting motion, with opposed bayonet slots 162 in a cap portion 150 of known nipple assembly 110 of any desired construction.

Known nipple assembly 110 includes an elongated, generally tubular body 126 which may be provided with hexagonal outer, flat, surface portions 136, if so desired. An inner end of body 126 is provided with an annular end surface 128 having a central aperture 130 and an inner frusto-conically tapered portion 132. In addition, body 126 includes a through bore 134 and is provided with an apertured valve guide 138, in bore 134 that serves to seat one end of a known or conventional valve assembly 140, similar to those of valve assemblies 28 and 28', which, in the interest of brevity, will not be discussed further. Suffice it to say, head portion 142 of valve 140 extends through central aperture 130 akin to that of head portion 76 of valve 28, as best seen in FIG. 4.

Body flat surface portions 136 also include a peripheral recess 146 that serves, in conjunction with at least one metal retainer ring 148, to axially and circumferentially retain an inner annular end portion 152 of a peripheral cup member 150 that surrounds the inner end portion 144 of body 126. Annular end portion 152 is provided with a plurality of preferably evenly peripherally spaced ventilating holes 156. Cup member 150 also includes a generally cylindrical portion 160 on its open inner end, with portion 160 being attached to annular end portion 152 at one end. Cylindrical portion 160 is provided with at least one and preferably with a pair of opposed bayonet slots 162 as well as a pair of opposed, elongated, slots 164, which function as thermal breaks that are axially spaced from bayonet slots 162. It should be evident from the noted drawings, particularly form FIGS. 7 and 8, that the inside diameter 166 of cylindrical portion 160 is sized for a slip fit relationship with maximum diameter portion 122 of coupler sleeve 26'.

In terms of the operation of coupler 20', as best seen in FIGS. 6 and 8, the male half or nipple assembly 110, specifically, inner end portion 144 thereof, is inserted into coupler sleeve inlet diameter portion 90' and makes sealing contact with the inner diameter of annular seal member 86. During this insertion, both internal valves 28' and 140 are opened via the abutments of their respective heads 76' and 142, in the manner already previously described. Although not shown in FIGS. 5-8, it should be understood that a further bayonet slot (not shown) can be provided, in cup member 150, to accommodate a vent fitting 32' (not shown), if so desired. In addition, if deemed necessary, one or both of surfaces 166 and 122 can be provided with a coating or band of a polymer material, such as PTFE or the like, in order to minimize the possibilities of ice formation and subsequent freezing therebetween.

Again, it should be understood that illustrated nipple assembly 110 is merely representative of the types of nipple assemblies that can be utilized and interchanged with couplers 20 and 20' and forms no part of the present invention. There is no presently known standard (such as ISO or ANSI, etc.) for the nipple profile set forth herein. Similarly, although while a bayonet-type of mechanical coupling is shown and described, other types of known couplings, if a mechanical coupling is desired, may be utilized.

It should further be understood that the operative interconnection between coupler 20 or coupler 20' with a male nipple assembly, such as 110, that this operative interconnection includes the insertion of nipple inner end portion 144 into coupler sleeve inlet portion 90 and/or 90' and makes sealing contact with the inner peripheral surface of annular interface seal 86 and, importantly so, severed tubular bushing 30, by virtue of its limited amounts of both axial and radial movements, within first cavity 36, aids in the prevention of icing, at the noted sealing contact, during the cryogenic liquid fluid transfer operation. In addition, these radial and axial movements of bushing 30 allows bushing 30 to move and/or expand over nipple inner end portion 144 (and/or any ice buildup thereon) while being disconnected from coupler 90 and/or 90'.

It is deemed that one of ordinary skill in the art will readily recognize that the several embodiments of the present invention fill remaining needs in this art and will be able to affect various changes, substitutions of equivalents and various other aspects of the invention as described herein. Thus, it is intended that the protection granted hereon be limited only by the scope of the appended claims and their equivalents.

What is claimed is:

1. A quick disconnect coupler, operatively interconnected with a cryogenic fluid transfer apparatus, said coupler comprising in combination:
   a. a generally cylindrical coupler body having a through bore and a front cylindrical portion with a first cavity open on one end, separated from a rear portion with a second cavity open on another end, via an apertured intermediate wall portion perpendicular on a first side facing said first cavity and including a tapered wall portion on a second side facing said second cavity;
   b. said first cavity having an inner peripheral surface surrounding an outer peripheral surface of a laterally severed tubular bushing, with the condition of being severed permitting a predetermined amount of radial expansion and contraction of said bushing;
   c. a generally tubular adaptor having a second through bore and a cylindrical rear portion, operatively attached to said cryogenic fluid transfer apparatus, a cylindrical, apertured, intermediate portion including a valve guide, located in said through bore, and a cylindrical front portion sealingly, operatively, connected with to said coupler body rear portion;
   d. an annular interface seal, spaced from said coupler body intermediate wall portion, said spacing of said seal permitting a limited amount of axial movement of said tubular bushing;
   e. a valve, normally biased to a closed position, interposed between said valve guide and said coupler body tapered wall portion, with a valve head portion shutting said apertured intermediate wall portion in the closed position thereof; and
   f. a generally tubular coupling sleeve having a frusto-conical front inlet portion separated from a cylindrical outlet portion via an annular end face adjoining said front inlet portion, said coupling sleeve being operatively secured to said coupler body front portion, with said annular end face physically abutting said first cavity.

2. The quick disconnect coupler of claim 1, wherein said severed tubular bushing is comprised of a polymeric composition material.

3. The quick disconnect coupler of claim 2, wherein said polymer composition material is comprised of a PTFE composition material.

4. The quick disconnect coupler of claim 2, wherein said polymer composition material is comprised of a PTFE equivalent material composition.

5. The quick disconnect coupler of claim 1, wherein said tubular bushing is severed from one peripheral edge to the other peripheral edge in a diagonal manner.

6. The quick disconnect coupler of claim 1, wherein said tubular bushing is scarf-cut.

7. The quick disconnect coupler of claim 1, wherein the outside diameter of said tubular bushing is radially spaced, a predetermined distance, from the inner peripheral surface of said first cavity, so as to permit a predetermined amount of radial movement therebetween.

8. The quick disconnect coupler of claim 1, wherein said frusto-conical front inlet portion of said coupling sleeve further includes a radial aperture.

9. The quick disconnect coupler of claim 8, wherein said aperture is operatively connected with one end of a vent fitting, with another end of said fitting being in an operative connection with a cryogenic fluid storage tank of a cryogenic device associated with said cryogenic fluid transfer apparatus.

10. The quick disconnect coupler of claim 9, wherein said operative connection with said cryogenic fluid storage tank includes a flow control valve.

11. The quick disconnect coupler of claim 10, wherein said flow control valve is associated with said cryogenic fluid storage tank.

12. The quick disconnect coupler of claim 9, wherein said operative connection with said cryogenic fluid storage tank is at a position in said tank that is filled with a gaseous fluid.

13. The quick disconnect coupler of claim 9, wherein said operative connection of said coupling sleeve front inlet portion with said cryogenic fluid storage tank of said cryogenic device permits the purging of said inlet portion by utilizing said cryogenic device's own gaseous fluid as the purge mechanism, in the form of a moisture remover, during said cryogenic liquid fluid transfer operation.

14. The quick disconnect coupler of claim 1, further including a male nipple assembly releasably joined with said coupler via an operative interconnection.

15. The quick disconnect coupler and male nipple assembly of claim 14, wherein said operative interconnection includes, in said nipple assembly, an inner end portion adapted to be inserted into said coupler via said coupler sleeve inlet portion and making a sealing contact with the inner peripheral surface of said annular interface seal, said severed tubular bushing, via said limited amounts of axial and radial movements, aiding in the prevention of icing, at said sealing contact, during said cryogenic liquid fluid transfer operation.

16. The quick disconnect coupler and male nipple assembly of claim 14, wherein said coupling front inlet portion further includes a radial aperture, said aperture being operatively interconnected with one end of a vent fitting, with another end of said vent fitting, in turn, being in an operative interconnection with a cryogenic fluid storage vessel of a cryogenic device associated with said cryogenic fluid transfer apparatus.

17. The quick disconnect coupler and male nipple assembly of claim 16, wherein said operative interconnection of said coupling sleeve inlet portion with said cryogenic fluid storage vessel permits the purging of said inlet portion and the adjacent nipple inner end portion by utilizing said cryogenic device's own gaseous fluid as the purging medium, in the form of moisture removal, during said cryogenic liquid fluid transfer operation.

18. The quick disconnect coupler and male nipple assembly of claim 14, wherein said operative interconnection further includes, in the outer peripheral surface of one of said coupling sleeve, at least one radially outwardly-directed, cylindrical, pin, said at least one pin being adapted to releasably mate, in a twisting motion, with one of at least one bayonet slot, formed in a cup member concentric and connected with said nipple assembly inner end portion.

19. The quick disconnect coupler and male nipple assembly of claim 14, wherein said operative interconnection with said cryogenic fluid storage vessel is at a position in said vessel that is filled with the gaseous phase of the cryogenic liquid fluid therein.

20. A quick disconnect coupler, operatively interconnected with a cryogenic fluid transfer apparatus, said coupler comprising in combination:
  a. a generally cylindrical coupler body having a through bore and a front cylindrical portion with a first cavity open on one end, separated from a rear portion with a second cavity open at another end, via an apertured intermediate wall portion perpendicular on a first side facing said first cavity and including a tapered wall portion on a second side facing said second cavity;
  b. said first cavity surrounding an outer peripheral surface of a tubular bushing;
  c. an annular interface seal, located at one axial end of said bushing, permitting a limited amount of axial movement of said bushing;
  d. a generally tubular adaptor having a second through bore and a cylindrical rear portion, operatively attached to said cryogenic fluid transfer apparatus, a cylindrical, apertured, intermediate portion including a valve guide, located in said through bore, and a cylindrical front portion sealingly, operatively, connected to said body rear portion;
  e. a valve, normally biased to a closed position, interposed between said valve guide and said coupler body tapered wall portion, with a valve head portion shutting said apertured intermediate wall portion in said closed position;
  f. a generally tubular coupling sleeve having a frusto-conical front inlet portion separated from a cylindrical outlet portion via an annular end face adjoining said front inlet portion, said coupling sleeve being operatively secured to said coupler body front portion, with said annular end face physically abutting said first cavity; and
  g. a vent fitting having one end thereof connected with said radial aperture and another end thereof being in an operative connection with a cryogenic fluid storage vessel associated with said cryogenic fluid transfer apparatus, wherein said operative connection permits purging of said inlet portion by utilizing said cryogenic vessel's own gaseous phase as a purging medium, for moisture removal, during said transfer operation.

21. The quick disconnect coupler of claim 20, wherein said operative connection between said coupler and said cryogenic fluid storage vessel includes a flow control valve.

22. The quick disconnect coupler of claim 21, wherein said flow control valve is associated with said cryogenic fluid storage vessel.

23. The quick disconnect coupler of claim 20, wherein said operative connection with said cryogenic fluid storage vessel is at a position in said vessel that is filled with a gaseous phase of said cryogenic fluid.

24. The quick disconnect coupler of claim 20, further including a male nipple assembly releasably joined with said coupler via a further operative interconnection.

25. The quick disconnect coupler of claim 24, wherein said further operative connection includes, in said nipple assembly, an inner end portion adapted to be inserted into said coupler via said coupler sleeve inlet portion and making a sealing contact with the inner peripheral surface of said annular interface seal.

26. The quick disconnect coupler of claim 25, wherein said further operative interconnection permits the purging of said inlet portion and the adjacent nipple inner end portion.

27. The quick disconnect coupler of claim 24, wherein said tubular bushing is severed from one peripheral edge to the other peripheral edge in other than a direct lateral cut.

28. The quick disconnect coupling of claim 27, wherein said tubular bushing is scarf-cut, said cut aiding in the prevention of icing at a sealing contact between the inner peripheral surface of said annular interface seal and said adjoining male nipple portion.

29. The quick disconnect coupling of claim 27, wherein said scarf-cut tubular bushing is comprised of a polymeric material of one of a PTFE composition and a PTFE equivalent composition.

30. The quick disconnect coupling of claim 27, wherein the outside diameter of said severed tubular bushing is radially spaced, a predetermined distance, from the inner peripheral surface of coupler body first cavity, so as to permit a predetermined amount of radial movement therebetween.

* * * * *